United States Patent [19]

Tsuchihashi et al.

[11] 4,242,522
[45] Dec. 30, 1980

[54] O-(N-ALLYL-2,6-DICHLOROANILINO)-PHENYLACETIC ACID DERIVATIVE AND A PROCESS FOR PREPARING THE SAME

[75] Inventors: Genichi Tsuchihashi, Tama; Katsuyuki Ogura, Sagamihara; Ryozo Sakoda, Funabashi; Isao Hashiba, Funabashi; Shuichi Fukushima, Funabashi, all of Japan

[73] Assignees: Nissan Chemical Industries, Ltd.; Sagami Chemical Research Center, both of Tokyo, Japan

[21] Appl. No.: 75,909

[22] Filed: Sep. 17, 1979

[30] Foreign Application Priority Data

Sep. 27, 1978 [JP] Japan .................. 53/118026

[51] Int. Cl.³ .................. C07C 101/453; C07C 83/10; C07C 103/28
[52] U.S. Cl. .................. 560/47; 260/500.5 H; 564/163; 562/456
[58] Field of Search .................. 260/500.5 H, 558 A; 560/47; 562/456

[56] References Cited

U.S. PATENT DOCUMENTS

| | | | |
|---|---|---|---|
| 3,511,872 | 5/1970 | Sherlock | 560/47 |
| 3,558,690 | 1/1971 | Sallmann et al. | 560/47 |
| 4,173,577 | 11/1979 | Sallmann et al. | 260/500.5 H |

OTHER PUBLICATIONS

Nohara, Chem. Absts., 86, 43412(d), 1977.

Sallmann et al., Chem. Absts., 77, 19403(v), 1972.

*Primary Examiner*—G. T. Breitenstein
*Attorney, Agent, or Firm*—Frishauf, Holtz, Goodman & Woodward

[57] ABSTRACT

An o-(N-allyl-2,6-dichloroanilino)phenylacetic acid derivative represented by the formula:

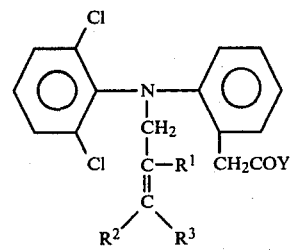

wherein $R^1$, $R^2$ and $R^3$, which may be the same or different, individually represent a hydrogen atom, a halogen atom or an alkyl group; Y represents a hydroxyl group, an alkoxyl group, a —$OM^1$ group in which $M^1$ is an alkali metal atom, a —$OM_{\frac{1}{2}}^2$ group in which $M^2$ is an alkaline earth metal atom, an amino group having the formula —$NR^5R^6$ in which $R^5$ and $R^6$, which may be the same or different, individually represent a hydrogen atom or an alkyl group, or a hydroxylamino group, and processes for preparing the same.

14 Claims, No Drawings

O-(N-ALLYL-2,6-DICHLOROANILINO)PHENYLACETIC ACID DERIVATIVE AND A PROCESS FOR PREPARING THE SAME

This invention relates to a novel o-(N-allyl-2,6-dichloroanilino)phenylacetic acid derivative and a process for preparing the same. More particularly, this invention relates to a novel o-(N-allyl-2,6-dichloroanilino)phenylacetic acid derivative which is useful as an intermediate for sodium salt of o-(2,6-dichloroanilino)phenylacetic acid (Diclofenac sodium) being known to be a useful medicament showing anti-inflammatory and analgesic activities [P. J. Krupp et al, Experimentia, p. 450 (1973)].

For the preparation of o-(2,6-dichloroanilino)-phenylacetic acid, there have been heretofore proposed the following processes.

(1) Process through alkali-hydrolysis of N-(2,6-dichlorophenyl)indolinone

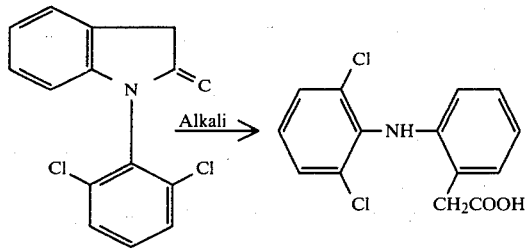

(U.S. Pat. No. 3,558,690 corresponding to Japanese Patent Publication No. 23418/1967)

(2) Process through alkali-hydrolysis of o-(2,6-dichloroanilino)benzyl cyanide

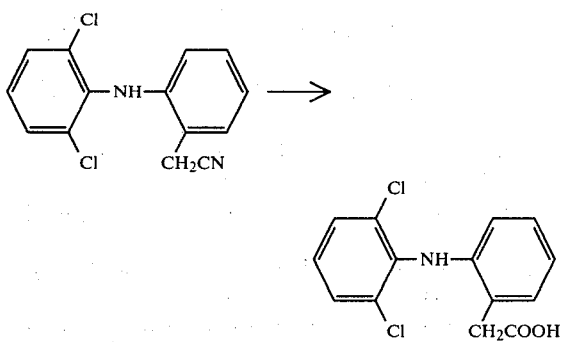

(U.S. Pat. No. 3,558,690 corresponding to Japanese Patent Publication No. 27374/1969)

(3) Process through reaction of o-(2,6-dichloroanilino)acetophenone with sulfur and morpholine to form the corresponding morpholide and subsequent hydrolysis of the latter

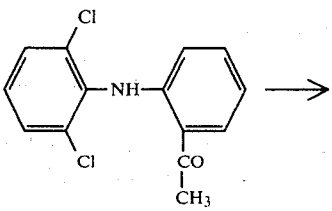

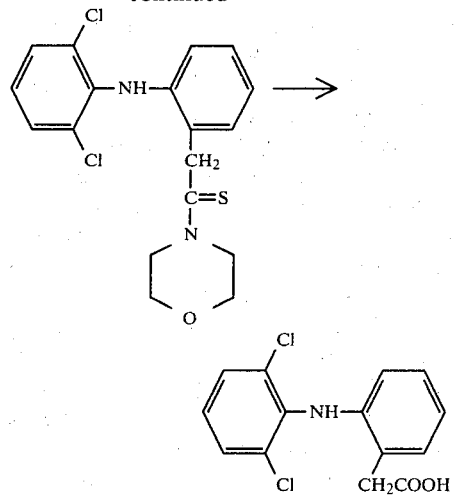

(British Pat. No. 1,183,968 corresponding to Japanese Patent Publication No. 27573/1969)

These prior art processes have proposed to utilize various different starting compounds and more detailed studies on the preparation of such starting compounds have revealed that N-(2,6-dichlorophenyl)anthranilic acid is used as an intermediate material in every process. More specifically, the starting material in Process (1), N-(2,6-dichlorophenyl)indolinone, can be produced by reaction of 2,6-dichlorodiphenylamine with chloroacetyl chloride, while it has been proposed to produce 2,6-dichlorodiphenylamine by decarboxylation of N-(2,6-dichlorophenyl)anthranilic acid with thermal decomposition.

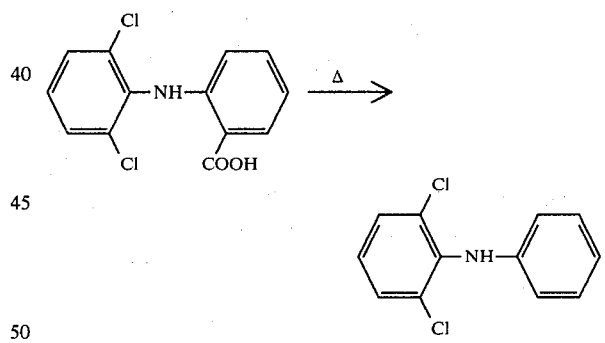

In Process (2), o-(2,6-dichloroanilino)benzyl cyanide is synthesized by reduction of N-(2,6-dichlorophenyl)anthranilic acid with lithium aluminum hydride to form o-(2,6-dichloroanilino)benzyl alcohol, conversion of the latter to the corresponding halide and subsequent reaction with sodium cyanide. The starting material of Process (3), o-(2,6-dichloroanilino)acetophenone, is prepared from the acid chloride of N-(2,6-dichlorophenyl)anthranilic acid. In short, all prior art processes given hereinabove have employed as an intermediate material N-(2,6-dichlorophenyl)anthranilic acid and prepared therefrom o-(2,6-dichloroanilino)phenylacetic acid through multi-stage, complicated steps. Further, the intermediate material, N-(2,6-dichlorophenyl)anthranilic acid is synthesized by the so-called Ullmann reaction wherein a 2-halobenzoic acid or 2,6-dichloro-1-bromobenzene is subjected to reaction with 2,6- dichloroaniline or anthranilic acid respectively in the presence of a copper catalyst, but this reaction provides an extremely low yield. Accordingly, the process using this intermediate material can be said to be commercially highly disadvantageous.

Then, the present inventors have made earnest studies to develop a process for the preparation of Diclofenac sodium with easier procedures and less steps from N-(2,6-dichlorophenyl)anthranilaldehyde, which can be prepared in a high yield from 2,6-dichloroaniline and a 2-halobenzaldehyde easily available in a commercial scale in accordance with the process of Japanese Patent Provisional Publication No. 95533/1979. As a result, the inventors have attained a new and commercially advantageous process through the present compound and completed this invention.

An object of this invention is to provide a novel o-(N-allyl-2,6-dichloroanilino)phenylacetic acid derivative which is useful as an intermediate for sodium salt of o-(2,6-dichloroanilino)phenylacetic acid (Diclofenac sodium).

Another object of this invention is to provide a process for preparing the o-(N-allyl-2,6-dichloroanilino)phenylacetic acid derivative.

The present compound, i.e., the o-(N-allyl-2,6-dichloroanilino)phenylacetic acid derivative is represented by the formula:

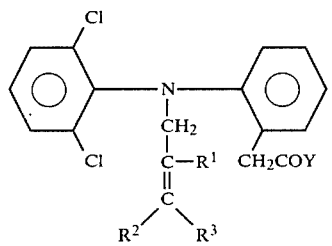

wherein $R^1$, $R^2$ and $R^3$, which may be the same or different, individually represent a hydrogen atom, a halogen atom or an alkyl group; Y represents a hydroxyl group, an alkoxyl group, a —$OM^1$ group in which $M^1$ is an alkali metal atom, a —$OM_{\frac{1}{2}}^2$ group in which $M^2$ is an alkaline earth metal atom, an amino group having the formula —$NR^5R^6$ in which $R^5$ and $R^6$, which may be the same or different, individually represent a hydrogen atom or an alkyl group, or a hydroxylamino group.

The halogen atom includes chlorine, bromine and iodine. The alkyl group represented by $R^1$, $R^2$ and $R^3$ may preferably be an alkyl group of 1 to 4 carbon atoms, e.g., methyl, ethyl, propyl and butyl. The alkoxyl group represented by Y may preferably be an alkoxyl group of 1 to 4 carbon atoms, e.g., methoxy, ethoxy, propoxy and butoxy. $M^1$ includes lithium, sodium and potassium. $M^2$ includes barium, calcium and magnesium. The alkyl group represented by $R^5$ and $R^6$ may preferably be an alkyl group of 1 to 4 atoms, e.g., methyl, ethyl, propyl and butyl.

As the concrete examples of the present compounds, there may be mentioned the following.
(1) o-(N-allyl-2,6-dichloroanilino)phenylacetic acid
(2) o-(N-methallyl-2,6-dichloroanilino)phenylacetic acid
(3) o-[N-(2-butyl-2-propen-1-yl)-2,6-dichloroanilino]phenylacetic acid
(4) o-(N-crotyl-2,6-dichloroanilino)phenylacetic acid
(5) o-[N-(2-penten-1-yl)-2,6-dichloroanilino]phenylacetic acid
(6) o-[N-(2-hexen-1-yl)-2,6-dichloroanilino]phenylacetic acid
(7) o-[N-(2-hepten-1-yl)-2,6-dichloroanilino]phenylacetic acid
(8) o-[N-(3-chloro-2-buten-1-yl)-2,6-dichloroanilino]phenylacetic acid
(9) o-[N-(3-chloro-2-buten-1-yl)-2,6-dichloroanilino]phenylacetic acid
(10) lithium o-(N-allyl-2,6-dichloroanilino)phenylacetate
(11) sodium o-(N-allyl-2,6-dichloroanilino)phenylacetate
(12) potassium o-(N-allyl-2,6-dichloroanilino)phenylacetate
(13) magnesium o-(N-allyl-2,6-dichloroanilino)phenylacetate
(14) barium o-(N-allyl-2,6-dichloroanilino)phenylacetate
(15) calcium o-(N-allyl-2,6-dichloroanilino)phenylacetate
(16) methyl o-(N-allyl-2,6-dichloroanilino)phenylacetate
(17) ethyl o-(N-allyl-2,6-dichloroanilino)phenylacetate
(18) propyl o-(N-allyl-2,6-dichloroanilino)phenylacetate
(19) butyl o-(N-allyl-2,6-dichloroanilino)phenylacetate
(20) methyl o-(N-methallyl-2,6-dichloroanilino)phenylacetate
(21) methyl o-(N-crotyl-2,6-dichloroanilino)phenylacetate
(22) methyl o-[N-(3-chloro-2-buten-1-yl)-2,6-dichloroanilino]phenylacetate
(23) o-(N-allyl-2,6-dichloroanilino)phenylacetamide
(24) N-propyl-o-(N-allyl-2,6-dichloroanilino)phenylacetamide
(25) N,N-dimethyl-o-(N-allyl-2,6-dichloroanilino)phenylacetamide
(26) N,N-diethyl-o-(N-allyl-2,6-dichloroanilino)phenylacetamide
(27) N,N-dipropyl-o-(N-allyl-2,6-dichloroanilino)phenylacetamide
(28) N,N-dibutyl-o-(N-allyl-2,6-dichloroanilino)phenylacetamide
(29) o-(N-allyl-2,6-dichloroanilino)phenylacetohydroxamic acid The process for preparing the present compound [I] may be illustrated by the reaction schema as shown below.

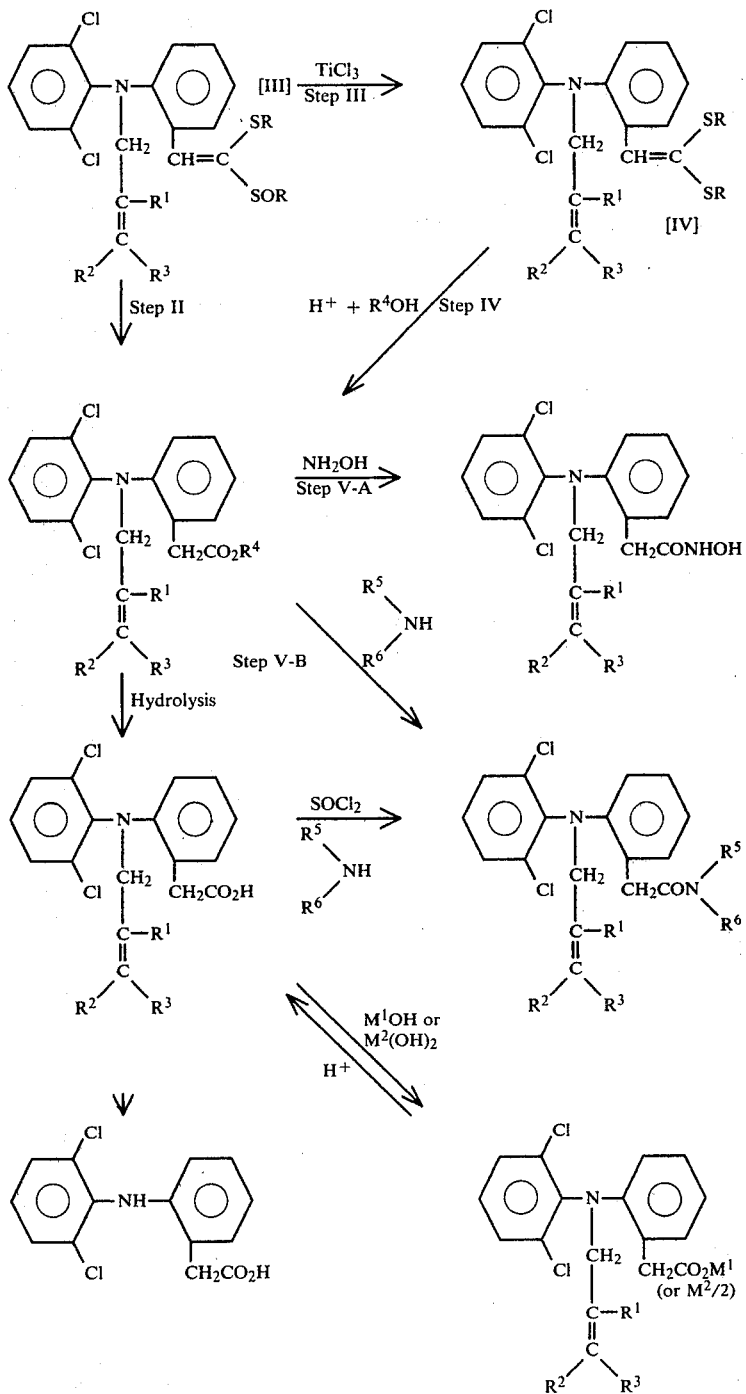
(wherein X is a chlorine atom or a bromine atom; R is an alkyl group, preferably an alkyl group of 1 to 4 carbon atoms, e.g., methyl, ethyl, propyl, butyl and the like; $R^4$ is an alkyl group, preferably an alkyl group of 1 to 4 carbon atoms, e.g., methyl, ethyl, propyl and butyl; and $R^1$, $R^2$, $R^3$, $R^5$ and $R^6$ are the same as defined above).

Step I

The Step I involves to react the aldehyde having the above general formula [II], in the presence of an alkali metal halide, with an allyl halide derivative having the general formula [V]:

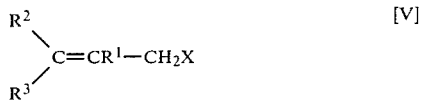

(wherein X is chlorine or bromine) to produce a compound having the general formula [VI]:

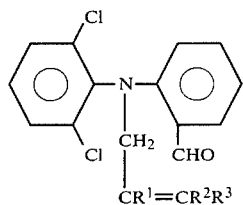

and subsequently with a formaldehyde dialkylmercaptal-S-oxide having the general formula [VII]:

(wherein R is as defined above) to produce the desired compound of the general formula [III]. As the compound [VII], formaldehyde dimethylmercaptal-S-oxide is preferred.

Every reaction is conducted in the presence of a solvent and it is particularly preferred to effect the reaction in an aprotic polar solvent since the reaction may proceed more smoothly. Examples of the aprotic polar solvent may include dimethylformamide (DMF), dimethyl sulfoxide, tetramethyl urea, tetrahydrofuran and the like and the aprotic polar solvent may be employed in admixture with a hydrocarbon that does not directly participate in the reaction such as benzene, toluene or xylenes. Examples of the alkali metal hydride may include sodium hydride, potassium hydride, lithium hydride and the like. Sodium hydride is particularly preferable in view of economy and easiness in reaction. The alkali metal hydride may be usually employed in about 2 molar equivalents to the starting compound [II], but it may be used at a higher level. The alkali metal hydride may be added all at once when the reaction begins, but it would tend to give the desired compound in a higher yield and a better reproducibility that the hydride is applied in several divided portions.

In carrying out every reaction, the reaction may proceed smoothly at a temperature of 0°–70° C. and preferably at 0°–40° C. because of easier procedures.

Step II

The Step II is to convert the compound of the above general formula [II] obtained in the Step I into the o-(N-allyl-2,6-dichloroanilino)phenylacetic acid ester represented by the general formula [I] wherein Y is an alkoxyl group.

In this Step, it is essential to react the compound of the above general formula [III] with an alcohol ($R^4OH$) in the presence of a mineral acid. As the mineral acid, there may be mentioned hydrochloric acid, hydrobromic acid, sulfuric acid, phosphoric acid and the like acids known in the art and hydrohalic acids such as hydrochloric acid (including hydrogen chloride) and hydrobromic acid are particularly preferable as the reaction may proceed smoothly. As the alcohols, there may be employed such alcohols commonly used in the art as methanol, ethanol, propanol or butanol and may act also as a solvent when employed in an excess amount.

Also, benzene, toluene, tetrahydrofuran and the like, if it does not participate directly in the reaction, may be used as a solvent, if desired. In carrying out this Step, the reaction may sufficiently proceed at room temperature and tends to be promoted by heating.

Step III

The ester of formula [I] ($Y=OR^4$) can be derived from compound [III] by another process (Step III) in which compound [III] is reduced to produce once a 1,1-bis (alkylthio)-2-[o-(N-allyl-2,6-dichloroanilino)-]ethylene represented by formula [IV] and then the so produced compound [IV] is converted into the ester of formula [I] ($Y=OR^4$).

In this step, it is essential to use a reagent which can reduce the sulfenyl group into sulfide. Although there have conventionally been known, as the reagent capable of reducing a sulfoxide into a sulfide, phosphorous trichloride, titanium trichloride, diethyl phosphate disulfide, lithiumaluminum hydride, a combination of stannous chloride and hydrogen chloride, and the like, it has never been known any reactions in which these reagents were used to derive novel compound [IV] from compound [III]. Since the compound [III] has a complicated molecular structure, the desired compound can not be obtained in a satisfactory yield even when lithium aluminum hadride or phosphorus trichloride is used for the reaction. As a result of the extensive studies by the present inventors, it was found that the use of titanium trichloride or a metal salt containing titanium trichloride promotes smoothly the reaction to yield the desired compound [III] quantitatively. In the reduction reaction by titanium trichloride or a metal salt containing titanium trichloride, the use of around two mole equivalents (two reduction equivalents) of titanium trichloride is sufficient and more than two equivalents thereof may be used. In the present reaction, it is preferable to use a solvent which does not participate in the reaction. As the solvent, there may be exemplified chloroform, methylene chloride, methanol and benzene. While the reaction proceeds at −20° to 80° C., it may be preferred to carry out the reaction at 0° to 30° C.

Step IV

In this step, it is essential to react the compound of the above general formula [IV] with an alcohol ($R^4OH$) in the presence of an acid. As the acid, there may be used a mineral acid such as hydrochloric acid, sulfuric acid, phosphoric acid, etc., and an organic acid such as trichloroacetic acid, trifluoroacetic acid, trifluoromethanesulfonic acid, p-toluene sulfonic acid, etc. As the alcohols, there may be employed such alcohols commonly used in the art as methanol, ethanol, propanol or butanol and may act also as a solvent when employed in an excess amount.

Also, benzene, toluene, tetrahydrofuran and the like, if it does not participate directly in the reaction, may be used as a solvent, if desired. In carrying out this Step, the reaction may sufficiently proceed at room temperature and tends to be promoted by heating.

Titanium trichloride or a metal salt containing titanium trichloride, which is used in Step III, may also be employed as the acid for the purpose of obtaining compound [I] ($Y=OR^4$) from the so obtained compound [IV]. Therefore, when water or an alcohol is used as a solvent in Step III, it is unnecessary to isolate compound [IV] but the desired compound [I] ($Y=OR^4$) can be derived directly by heating the intermediate reaction mixture as such. This procedure belongs to an embodiment of this invention.

The ester of formula [I] ($Y=OR^4$), which is obtained by the above-mentioned Steps II, III and IV, can be converted into a hydroxamic acid [I] ($Y=-NHOH$) or an amide [I] ($Y=-NR^5R^6$) by way of a process known to a person skilled in the art, as follows.

Step V-A

This step is a step in which the ester of formula [I] ($Y=OR^4$) is converted into a hydroxamic acid [I] ($Y=-NHOH$). In this step, it is essential to react compound [I] ($Y=OR^4$) with hydroxylamine or a salt thereof in a solvent in the presence of a base. As the solvent may be used, for example, diethyl ether, tetrahydrofuran, etc., which do not participate directly in the reaction. In order to carry out the reaction smoothly, the use of an alcohol is preferred. As the base may preferably be used an sodium alkoxide and an alkali metal hydroxide. Among the combinations of an alcohol and a base used in the reaction of compound [I] ($Y=OR^4$), a combination of an alcohol $R^4OH$ and a sodium alkoxide $R^4ONa$ is particularly preferred.

Step V-B

This step is to convert ester [I] ($Y=OR^4$) into an amide [I] ($Y=NR^5R^6$). In this step, it is essential to react the ester [I] ($R=OR^4$) with an amine $HNR^5R^6$ in a solvent. As the solvent may widely be used, for example, diethyl ether, tetrahydrofuran, etc., which do not participate in the reaction directly. In order to carry out the reaction smoothly, the use of an alcohol is preferred. As the amine of the formula $HNR^5R^6$, there may widely be employed, for example, ammonia, methylamine, dimethylamine, ethylamine, diethylamine, butylamine, dibutylamine, etc.

In cases where the amine has low boiling point as in the case of ammonia, it is preferable to carry out the reaction under pressure by using an autoclave.

The ester [I] ($Y=OR^4$), which is obtained in the above mentioned Steps III and IV, can easily be hydrolized under alkaline or basic conditions to afford o-(N-allyl-2,6-dichloroanilino)phenylacetic acid [I] ($Y=OH$), an alkali metal salt thereof or an alkaline earth metal salt thereof [I] ($Y=OM^1$ or $OM_{\frac{1}{2}}^2$, in which $M^1$ means an alkali metal atom, $M^2$ means an alkaline earth metal atom and $M_{\frac{1}{2}}^2$ means $\frac{1}{2}M^2$).

The thus obtained acid [I] ($Y=OH$) can be converted into an amide [I] ($Y=NR^5R^6$) by a method known to a person skilled in the art.

For instance, the compound [I] ($Y=OH$) is converted once into an acid chloride [I] ($Y=Cl$) by using a reagent capable of converting an acid into an acid chloride, such as thionyl chloride, phosphorus pentachloride, etc., and then the so formed acid chloride [I] ($Y=Cl$) is reacted with an amine $HNR^5R^6$ in a solvent to give an amide [I] ($Y=-NR^5R^6$). As the solvent may suitably be used benzene, toluene, diethyl ether, tetrahydrofuran, etc., which do not participate in the reaction directly.

As mentioned above, the compound [I] of this invention can be converted into o-(2,6-dichloroanilino)-phenylacetic acid by deallylation, i.e., by removing an allyl group represented by the formula:

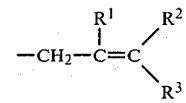

wherein $R^1$, $R^2$ and $R^3$ have the same meanings as defined above. The deallylation reaction easily proceeds in the presence of a novel metal catalyst. As the noble metal catalyst may be used a salt or a complex of palladium or rhodium which promotes the rearrangement of a carbon-to-carbon double bond. However, in the case of the present reaction, the use of rhodium trichloride is preferred on the view point of easy process of the reaction. As the solvent may be used benzene, toluene, ethyl ether, tetrahydrofuran, ethylene glycol dimethyl ether, methanol, ethanol, etc., and it may be preferable to carry out the reaction by adding water to the reaction system. While the reaction proceeds at room temperature, heating of the reaction system tends to promote the reaction. The reaction is carried out usually at 0° to 200° C., preferably at 50° to 130° C.

It should be noted that o-(2,6-dichloroanilino)-phenylacetohydroxamic acid, which can be derived by the deallylation of compound [I] ($Y=-NHOH$) of this invention, has also been known to show anti-inflammatory and analgesic activities as in the case of Dichlofenac sodium (British Pat. No. 1,331,181 corresponding to Japanese Patent Provisional Publication No. 6175/1972).

This invention will be explained in greater detail by way of the following examples and reference example.

[EXAMPLE 1]

Synthesis of 1-[o-(N-allyl-2,6-dichloroanilino)phenyl]-2-methylsulfinyl-2-methylthioethylene To a solution of 13.3 g. (0.05 mole) of N-(2,6-dichlorophenyl)anthranilaldehyde in 50 ml. of DMF were added gradually at 20°–30° C. 2.2 g. (0.05 mole) of 55% sodium hydride. After stirring below 20° C. over 30 minutes, 6.6 g. (0.055 mole) of allyl bromide were added dropwise under ice-cooling and stirring was continued below 10° C. for further 2 hours. Then, additional 2.7 g. (0.06 mole) of 55% sodium hydride were added thereto and 7.4 g. (0.06 mole) of formaldehyde dimethylmercaptal-S-oxide were added dropwise at 10–15° C. Stirring was continued at room temperature for 5 hours, a large amount of water was added and the mixture was left under cooling for 1 day. The crystalline substance thus separated was recovered by filtration, dried and finally recrystallized from n-hexane to give 15.2 g. of 1-[o-(N-allyl-2,6-dichloroanilino)- phenyl]-2-methylsulfinyl-2-methylthioethylene. Yield, 74%. M. P.: 104°–107° C.

The compound was identified by IR, NMR and elementary analysis.

IR(KBr) cm$^{-1}$: 1590, 1490, 1445, 1225, 1052, 796, 770, 738

NMR(CDCl$_3$)δ ppm: 1.99 (3H, s), 2.45 (3H, s), 4.28 (2H, dt, J=6 and 1.5 Hz), 5.04-5.32 (2H, m), 6.02 (1H, ddt, J=17, 10 and 6 Hz), 6.80-7.36 (7H, m), 7.61 (1H, diffused d, J=8 Hz)

Elementary analysis: (for C$_{19}$H$_{19}$NOCl$_2$S$_2$); Calcd. (%): C, 55.34; H, 4.64; N, 3.40; S, 15.55; Found (%): C, 55.61; H, 4.62; N, 3.50; S, 15.30.

[EXAMPLE 2]

Synthesis of methyl o-(N-allyl-2,6-dichloroanilino) phenylacetate

To a solution of 5 g. (0.012 mole) of 1-[o-(N-allyl-2,6-dichloroanilino)phenyl]-2-methylsulfinyl-2-methylthio-ethylene in 45 ml. of methanol were added 3 ml. of methanol saturated with hydrogen chloride and the resultant mixture was stirred for 3.5 hours. The reaction mixture was concentrated under reduced pressure and the residue was recrystallized twice from methanol of give 3.4 g. of methyl o-(N-allyl-2,6-dichloroanilino)phenylacetate. Yield, 80%. M. P.: 94°–95° C.

The compound was identified by IR, NMR and elementary analysis.

IR(KBr) cm$^{-1}$: 3060, 2900, 1730, 1598, 1494, 1435, 1225, 1154, 996, 920, 795, 770, 748

NMR(CDCl$_3$) δ ppm: 3.32 (2H, s), 3.39 (3H, s), 4.28 (2H, dt, J=6 and 1 Hz), 4.98-5.28 (2H, m), 5.95 (1H, ddt, J=17, 10 and 6 Hz), 6.80-7.32 (7H, m)

Elementary analysis: (for C$_{18}$H$_{17}$O$_2$NCl$_2$); Calcd. (%): C, 61.73; H, 4.89; N, 4.00; Found (%): C, 61.81; H, 4.84; N, 3.93.

[EXAMPLE 3]

Synthesis of o-(N-allyl-2,6-dichloroanilino)phenylacetic acid

To a solution of 12.8 g. of methyl o-(N-allyl-2,6-dichloroanilino)phenylacetate in 18 ml. of methanol were added 10 ml. of a 2 N aqueous solution of sodium hydroxide and the resultant mixture was heated under reflux for 6 hours. The methanol was distilled off under reduced pressure, 10 ml. of water were added to the residue and then the mixture was adjusted to pH 4 with dilute hydrochloric acid. The crystalline substance thus separated was recovered by filtration, dried and recrystallized from ether-hexane to give 2.3 g. of o-(N-allyl-2,6-dichloroanilino)phenylacetic acid. Yield, 83%. M. P.: 147.5°–148.5° C.

The compound was identified by IR, NMR and elementary analysis.

IR(KBr) cm$^{-1}$: 3100–2700, 1705, 1600, 1492, 1440, 1220, 920, 790, 770, 735

NMR(CDCl$_3$) δ ppm: 3.37 (2H, s), 4.28 (2H, diffused d, J=6 Hz), 5.15 (1H, diffused dd, J=15 and 1.5 Hz), 5.26 (1H, diffused dd, J=17 and 1.5 Hz), 5.84 (1H, ddt, J=17, 10 and 6 Hz), 6.78-7.30 (7H, m), 10.73 (1H, broad s)

Elementary analysis: (for C$_{17}$H$_{15}$O$_2$NCl$_2$); Calcd. (%): C, 60.73; H, 4.50; N, 4.17; Found (%): C, 60.72; H, 4.41; N, 4.10.

[EXAMPLE 4]

Synthesis of sodium salt of o-(N-allyl-2,6-dichloroanilino)phenylacetic acid

To a solution of 672 mg. of o-(N-allyl-2,6-dichloroanilino)phenylacetic acid in 6 ml. of ethanol was added dropwise an ethanolic solution of sodium hydroxide until the resultant mixture reached pH 9. The ethanol was distilled off under reduced pressure, the residue was thin-layer chromatographed (silica gel, developing solvent; hexane: acetone=1:1) and dried at 90°–100° C. under reduced pressure to afford 652 mg. of sodium salt of o-(N-allyl-2,6-dichloroanilino)phenylacetic acid. Yield, 91%. M.P.: 235°–256° C.

The compound was identified by IR.

IR(KBr) cm$^{-1}$: 3100–2700, 1570, 1490, 1430, 1380, 1222, 920, 790, 770, 745

[Reference example]

Synthesis of o-(2,6-dichloroanilino)phenylacetic acid

To a solution of 1.01 g. (0.003 mole) of o-(N-allyl-2,6-dichloroanilino)phenylacetic acid in 13 ml. of 1,2-dimethoxyethane were added 0.05 g. of rhodium chloride and 0.5 ml. of water and the resultant mixture was refluxed with stirring for 8 hours. The solvent was distilled off under reduced pressure, the residue was dissolved in benzene and then the solution was filtered and concentrated. The crystalline substance thus separated was recrystallized from toluene-hexane to give 0.64 g. of o-(2,6-dichloroanilino)phenylacetic acid. Yield, 72%.

The compound was identified by melting point, IR, NMR and mass spectrum(MS).

M.P.: 158°–159.5° C.

IR(KBr) cm$^{-1}$: 3320, 3050–2400, 1690, 1505, 1450, 1300, 930, 760, 733

NMR(CDCl$_3$) δ ppm: 3.82 (2H, s), 6.5-7.4 (8H, m)

Mass spectrum (20 eV) m/e: 297 (M$^+$+2, 46.7%), 296 (M$^+$+1, 12.1%), 295 (M$^+$, 71.2%), 279 (7.7%), 2.77 (11.4%), 244 (14.6%), 243 (7.7%) 242 (43.3%), 216 (36.7%), 215 (26.7%), 214 (base peak)

[EXAMPLE 5]

Synthesis of ethyl o-(N-allyl-2,6-dichloroanilino) phenylacetate

To a solution of 959 mg. of 1-methylsulfinyl-1-methylthio-2-]o-(N-allyl-2,6-dichloroanilino)phenyl]ethylene in 10 ml. of dry chloroform were added under ice-cooling 8.0 ml. (2.4 mmole) of an ethanolic solution of eutectic mixture of titanium trichloride and aluminium chloride (3TiCl$_3$.AlCl$_3$) and the resulting mixture was stirred for 30 minutes. After confirmation of the consumption of the starting material by means of TLC, the reaction mixture was heated under reflux for 5 hours.

After the ethanol was distilled off under reduced pressure, 50 ml. of water were added to the residue and then the mixture was extracted three times with 25 ml. of methylene chloride. The extract was washed once with 50 ml. of water and dried over anhydrous magnesium sulfate. The solvent was distilled off under reduced pressure to afford 776 mg. of a liquid, which was separated by means of column chromatography (silica gel, n-hexane:ether=4:1) to obtain 679 mg. of ethyl o-(N-allyl-2,6-dichloroanilino)phenylacetate as a pale yellow highly viscous liquid.

Yield: 81%

The compound was identified by IR, NMR and MS.

IR(neat) cm$^{-1}$: 3067, 2971, 2919, 1737, 1602, 1556, 1496, 1445, 1369, 1335, 1230, 1155, 1031, 923, 790, 775, 746

NMR(CDCl$_3$) δ ppm: 1.12 (3H, t, J=7 Hz), 3.32 (2H, s), 3.88 (2H, q, J=7 Hz), 4.30 (2H, dt, J=6 and 1 Hz), 5.07 (1H, ddd, J=10, 2.5 and 1 Hz), 5.17 (1H, ddd, J=17, 2.5 and 1 Hz), 5.99 (1H, ddt, J=17, 10 and 6 Hz), 6.80–7.42 (7H, m)

MS(70 eV) m/e: 367 (3%,M$^+$+4), 365 (17%,M$^+$+2), 363 (25%,M$^+$), 336 (17%),334 (28%), 292 (55%),290 (80%),278 (26%), 276 (42%),254 (43%), 214 (100%), 179 (29%), 91 (30%), 41 (26%),29 (45%)

[EXAMPLE 6]

Synthesis of o-(N-allyl-2,6-dichloroanilino)phenylacetamide

To 120 mg. of o-(N-allyl-2,6-dichloroanilino)-phenylacetic acid were added 0.1 ml. of thionyl chloride under ice-cooling and the resulting mixture was stirred for 19 hours at room temperature. After removal of the excess thionyl chloride by evaporation under reduced pressure, the residue was dissolved in 10 ml. of anhydrous benzene and ammonia gas was introduced thereto for 5 hours. The crystalline substance separated was collected by filtration and washed sufficiently with methylene chloride. The solvent was distilled off under reduced pressure and the residue was separated by column chromatography (silica gel, ethyl acetate:benzene=4:1) to afford 58 mg. of o-(N-allyl-2,6-dichloroanilino)phenylacetamide.

Yield: 48%.

M.P.: 120.5°–122° C.

IR(Nujol) cm$^{-1}$: 3452, 3130, 1670, 1595

NMR(CDCl$_3$) δ ppm: 3.18 (2H, s), 4.26 (2H, dt, J=6 and 1 Hz), 5.12 (1H, dt, J=10 and 1 Hz), 5.20 (1H, dt, J=17 and 1 Hz), 5.95 (1H, ddt, J=17, 10 and 6 Hz), 4.86–6.26 (2H, bs), 6.92–7.52 (7H, m)

[EXAMPLE 7]

Synthesis of o-(N-allyl-2,6-dichloroanilino)phenylacetohydroxamic acid

In the stream of argon were dissolved 1.18 g. of hydroxylamine hydrochloride in 20 ml. of anhydrous methanol. To the resulting solution were added 54.8 ml. of a methanolic solution of sodium methoxide (0.62 mmol/ml.) and then the sodium chloride separated was filtered off. In the filtrate were dissolved 4.0 g. of methyl o-(N-allyl-2,6-dichloroanilino)phenylacetate and the resulting mixture was heated under reflux for 21.5 hours. Upon adjustment of the reaction mixture to pH 7 with 5% aqueous acetic acid solution, the colorless crystalline substance was precipitated. After a small amount of water were added to the mixture and cooled for 4 hours, the resulting crystalline substance was collected by filtration to afford 3.98 g. of o-(N-allyl-2,6-dichloroanilino)phenylacetohydroxamic acid, which was then recrystallized from methylene chloride and n-hexane to give colorless leaflike crystals.

Yield: 99%.

M.P.: 149.5°–151.0° C.

IR(KBr) cm$^{-1}$: 3400, 3200, 3010, 2900, 1630, 1485, 1435, 1220, 1050, 980, 915, 780

NMR(CDCl$_3$)δ ppm: 3.20 (2H, s), 4.28 (2H, dt, J=6 and 1 Hz), 5.00–5.34 (2H, m), 5.70–6.22 (1H, m), 6.70–7.66 (7H, m)

MS (70 eV) m/e: 352 (3%, M$^+$+2), 350 (4%, M$^+$), 318 (11%), 293 (20%), 292 (37%), 291 (36%), 290 (58%), 288 (16%), 278 (21%), 277 (23%), 276 (35%), 274 (22% ), 262 (18%), 254 (31%), 242 (22%), 240 (23%), 239 (21%), 216 (37%), 215 (29%), 214 (100%), 179 (26%), 178 (20%), 130 (22%), 91 (26%), 89 (22%), 78 (21%), 77 (27%), 51 (23%), 43 (29%), 39 (31%)

Elementary analysis (for C$_{17}$H$_{16}$N$_2$O$_2$Cl$_2$): Calcd. (%): C, 58.13; H, 4.59; N, 7.98; Cl, 20.19; Found (%): C, 58.26; H, 4.68; N, 7.97; Cl, 20.04.

[EXAMPLE 8]

Synthesis of 1-methylsulfinyl-1-methylthio-2-[o-(N-crotyl-2,6-dichloroanilino)phenyl]ethylene To a solution of 13.3 g. of N-(2,6-dichlorophenyl) anthranylaldehyde in 50 ml. of dimethylformamide were gradually added 2.72 g. of 55%-sodium hydride at room temperature. After the resulting mixture was stirred under water-cooling for 30 minutes, 5.44 g. of crotyl chloride was added dropwise thereto and the resulting mixture was stirred for 2 hours and 40 minutes under water-cooling and further for 2 hours and 40 minutes at room temperature. Then, after 2.72 g. of 55%-sodium hydride were gradually added again to the mixture and the resulting mixture was stirred for 2 hours at room temperature, 7.44 g. of formaldehyde dimethyl mercaptal-S-oxide were added dropwise thereto and the stirring was continued for 23 hours at room temperature. The reaction mixture was poured into 500 ml. of water and the resulting crystals precipitated were washed sufficiently with water and n-hexane by turns and dried to afford 14.7 g. of 1-methylsulfinyl-1-methylthio-2-[o-(N-crotyl-2,6-dichloroanilino)-phenyl]ethylene as pale yellow crystals.

Yield: 69%.

M.P.: 134.0°–134.5° C. (recrystallized from methylene chloride-n-hexane)

IR(KBr) cm$^{-1}$: 3060, 2900, 2850, 1590, 1470, 1450, 1435, 1225, 1055, 965, 785, 770, 745

NMR(CDCl$_3$)δ ppm: 1.60 (3H, dt, J=4 and 1.5 Hz), 1.97 (3H, s), 2.42 (3H, s), 4.21 (2H, dq, J=3.5 and 1 Hz), 5.51 (1H, dq, J=15 and 4 Hz), 5.70 (1H, dt, J=15 and 3.5 Hz), 7.72–6.78 (8H, m)

Elementary analysis (for C$_{20}$H$_{21}$NOCl$_2$S$_2$): Calcd. (%): C, 56.33; H, 4.96; N, 3.29; S, 15.04; Cl, 16.63; Found (%): C, 56.20; H, 4.90; N, 3.28; S, 15.02; Cl, 16.62.

[EXAMPLE 9]

Synthesis of 1,1-bis(methylthio)-2-[o-(N-crotyl-2,6-dichloroanilino)-phenyl]ethylene In the stream of argon were dissolved 371 mg. of 1-methylsulfinyl-1-methylthio-2-[o-(N-crotyl-2,6-dichloroanilino)phenyl]ethylene in 3 ml. of dry chloroform.

To the resulting solution were added 3.0 ml. of a methanolic solution of titanium trichloride (1.0 mmol./ml.) under ice-cooling and the reaction was carried out for 1 hour. Then after addition of 10 ml. of chloroform, the mixture was washed three times with 5 ml. of water. After the organic layer was dried over anhydrous magnesium sulfate, the solvent was distilled off to afford 330 mg. of solid substance. According to the analysis by NMR, the thus obtained substance was found to be substantially pure 1,1-bis(methylthio)-2-[o-

(N-crotyl-2,6-dichloroanilino)phenyl]ethylene. The samples for the analysis were obtained as pale yellow crystals by recrystallization from ether-n-hexane-methylene chloride.

Yield: 92%.

M.P.: 94°–95° C.

IR(KBr) cm$^{-1}$: 3050, 3010, 2897, 2835, 1594, 1481, 1454, 1431, 1235, 960, 903, 788, 772 749, 737, 591, 504

NMR(CDCl$_3$)δ ppm: 1.62 (3H, dt, J=4 and 1 Hz), 2.05 (3H, s), 2.12 (3H, s), 4.20 (2H, dq, J=5 and 1 Hz), 5.36–5.90 (2H, m), 6.38 (1H, s), 6.78–7.42 (7H, m)

MS (70 eV) m/e: 394 (10%, M$^+$-CH$_3$), 308 (26%), 302 (12%), 292 (11%), 257 (46%), 214 (8%), 101 (100%), 55 (21%)

Elementary analysis (for C$_{20}$H$_{21}$NS$_2$Cl$_2$): Calcd. (%): C, 58.53; H, 5.16; N, 3.41; S, 15.62; Cl, 17.28; Found (%): C, 58.40; H, 5.20; N, 3.44; S, 15.42; Cl, 17.41.

[EXAMPLE 10]

Synthesis of methyl o-(N-crotyl-2,6-dichloroanilino)phenylacetate

To a solution of 174 mg. of 1,1-bis(methylthio)-2-[o-(N-crotyl-2,6-dichloroanilino)phenyl]ethylene in a mixture of 2 ml. of anhydrous methanol and 1 ml. of dry chloroform were added 1 ml. of methanol saturated with hydrogen chloride and the resulting mixture was stirred for 9 hours at a temperature of 50°–60° C. Upon removal of the solvent by distillation under reduced pressure, 159 mg. of a solid was obtained, which was then separated by means of column chromatography (silica gel, n-hexane:ether=4:1) to afford 113 mg. of methyl o-(N-crotyl-2,6-dichloroanilino)phenylacetate.

Yield: 73%.

The compound was identified by melting point, IR, NMR and mass spectrum. The samples for Elementary analysis were obtained by recrystallization from methylene chloride-ether-n-hexane as colorless crystals.

M.P.: 89°–90° C.

IR(KBr) cm$^{-1}$: 3055, 2997, 2941, 2910, 1731, 1602, 1498, 1456, 1436, 1352, 1263, 1223, 1195, 1120, 1082, 1023, 1014, 957, 923, 849, 823, 788, 782, 756, 739, 602

NMR(CDCl$_3$)δ ppm: 1.69 (3H, m), 3.33 (2H, s), 3.41 (3H, s), 4.22 (2H, m), 5.30–5.86 (2H, m), 6.84–6.44 (7H, m)

MS (70 eV) m/e: 367 (3%, M$^+$+4), 365 (14%, M$^+$+2), 363 (21%, M$^+$), 328 (16%), 320 (18%), 304 (13%), 279 (20%), 242 (40%), 216 (33%), 215 (25%), 214 (93%), 55 (67%)

Elementary analysis (for C$_{19}$H$_{19}$O$_2$NCl$_2$): Calcd. (%): C, 62.65; H, 5.26; N, 3.85; Cl, 19.46; Found (%): C, 62.58; H, 5.30; N, 3.84; Cl, 19.55.

[EXAMPLE 11]

Synthesis of methyl o-(N-crotyl-2,6-dichloroanilino)phenylacetate

To a solution of 211 mg. of 1-methylsufinyl-1-methylthio-2-[N-crotyl-o-(2,6-dichloroanilino)phenyl]ethylene in 2 ml. of methanol and 1 ml. of chloroform was added 1 ml. of methanol saturated with hydrogen chloride and the resulting mixture was stirred for 5 hours at 50° C. and further for 17 hours at room temperature. Upon removal of the solvent by distillation and analysis of the residue by means of NMR, it was found that 85 mg. of methyl o-(N-crotyl-2,6-dichloroanilino)phenylacetate was formed.

Yield: 47%.

[EXAMPLE 12]

Synthesis of o-(N-crotyl-2,6-dichloroanilino)phenylacetic acid

To a solution of 48 mg. of methyl o-(N-crotyl-2,6-dichloroanilino)phenylacetate in 1 ml. of ethanol was added a solution of 20.6 mg. of potassium hydroxide in 2 ml. of water and the resulting mixture was heated under reflux for 15 hours. After 1 ml. of 40%-hydrochloric acid was added to the reaction mixture, the resulting mixture was extracted four times with 10 ml. portions of methylene chloride and the extract was dried over anhydrous magnesium sulfate. The solvent was distilled off under reduced pressure to afford 47 mg. of a solid. Upon analysis of the solid by means of NMR, it was revealed that the solid was substantially pure o-(N-crotyl-2,6-dichloroanilino)phenylacetic acid. The yield was almost quantitative. The samples for Elementary Analysis were obtained by recrystallization from ether-n-hexane as colorless crystals.

M.P.: 176°–177.5° C.

IR(KBr) cm$^{-1}$: 3300–2200 (broad absorption by OH), 1712, 1600, 1430, 1228, 1130, 926, 786

NMR(CDCl$_3$)δ ppm: 1.58 (3H, m), 3.38 (2H, s), 4.22 (2H, m), 5.58 (2H, m), 6.80–7.30 (7H, m), 10.3 (1H, bs)

MS (70 eV) m/e: 353 (3%, M$^+$+4), 351 (13%, M$^+$+2), 349 (22%, M$^+$), 314 (12%), 306 (12%), 295 (18%), 242 (50%), 216 (34%), 215 (28%), 214 (87%), 55 (100%)

[EXAMPLE 13]

Synthesis of 1-methylsulfinyl-1-methylthio-2-[o-(N-methallyl-2,6-dichloroanilino)phenyl]ethylene According to the same precedure as in Example 7 except that methallyl chloride was used in place of crotyl chloride, 1-methylsulfinyl-1-methylthio-2-[o-(N-methallyl-2,6-dichloroanilino)phenyl]ethylene was obtained.

The compound was identified by IR, NMR and elementary analysis.

IR(neat) cm$^{-1}$: 3055, 2915, 2830, 1599, 1484, 1455, 1441, 1235, 1223, 1059, 899, 788, 739

NMR(CDCl$_3$)δ ppm: 1.73 (3H, diffused s), 1.96 (3H, s), 2.46 (3H, s), 4.18 (2H, diffused s), 4.92 (1H, m), 5.06 (1H, m), 6.70–7.76 (8H, m)

MS (70 eV) m/e: 427 (1%, M$^+$+2), 425 (2%, M$^+$), 364 (17%), 362 (25%), 322 (21%), 320 (31%), 316 (21%), 315 (27%), 314 (26%), 307 (25%), 259 (38%), 258 (21%), 257 (100%), 84 (31%), 49 (34%), 29 (22%)

[EXAMPLE 14]

Synthesis of methy o-(N-methallyl-2,6-dichloroanilino)phenylacetate

To a solution of 757 mg. of 1-methylsulfinyl-1-methylthio-2-[o-(N-methallyl-2,6-dichloroanilino)phenyl]ethylene in 10 ml. of dry chloroform were added 4.2 ml. (1.76 mmol) of a methanolic solution of eutectic mixture of titanium trichloride and aluminium chloride and the resulting mixture was stirred for 30 minutes under ice-cooling. After confirmation of the consumption of the starting material by means of TLC, the reaction mixture was heated under reflux for 5 hours. The methanol was distilled off under reduced pressure, 50 ml. of water were added to the residue, and then the mixture was extracted three times with 25 ml. of methylene chloride. The extract was washed once with 25 ml. of a saturated aqueous sodium chloride and dried over anhydrous magnesium sulfate. Then the solvent was distilled off under reduced pressure to afford a liquid, which was separated by means of column chlomatography (silica gel, ether-n-hexane=1:5) to afford 494 mg. of methyl o-(N-methallyl-2,6-dichloroanilino)phenylacetate. Yield: 76%

The compound was identified by IR and NMR.

IR(neat) cm$^{-1}$: 3060, 2936, 2902, 2831, 1738, 1602, 1493, 1455, 1434, 1338, 1219, 1155, 1016, 894, 787, 773

NMR(CDCl$_3$)δ ppm: 1.72 (3H, s), 3.42 (5H, s), 4.21 (2H, s), 4.86 (1H, diffused s), 5.01 (1H, diffused s), 6.84–7.38 (7H, m)

MS (70 eV) m/e: 367 (5%, M$^+$+4), 365 (20%, M$^+$+2), 363 (32%, M$^+$), 322 (24%), 320 (35%), 290 (26%), 276 (25%), 268 (38%), 216 (34%), 215 (20%), 214 (100%), 91 (26%), 78 (20%), 55 (24%), 45 (33%)

[EXAMPLE 15]

Synthesis of methyl o-(N-3-chloro-2-butenyl-2,6-dichloroanilino)phenylacetate

According to the same procedures as in Examples 7, 8 and 9 except that 3-chloro-2-butenyl chloride was used in place of crotyl chloride, methyl o-(N-3-chloro-2-butenyl-2,6-dichloroanilino)phenylacetate was obtained as a final product.

The product was identified by IR, NMR and MS.

IR(neat) cm$^{-1}$: 3050, 3010, 2930, 2905, 2830, 1740, 1602, 1557, 1495, 1460, 1446, 1434, 1340, 1155, 1123, 788, 775, 744

NMR(CDCl$_3$)δ ppm: 1.97 (Z) and 2.03 (E) (3H in total, individually q, individually J=1H), 3.25 (E) and 3.31 (Z) (2H in total, individually s), 340 (3H, s), 4.38 (2H, m), 5.66 (E) and 5.86 (Z) (1H in total, individually td, individually J=12 and 1 Hz), 6.84–7.56 (7H, m)

MS (70 eV) m/e: 399 (3%, M$^+$+2), 397 (3%, M$^+$), 364 (32%), 362 (47%), 278 (21%), 242 (28%), 216 (34%), 215 (24%), 214 (100%), 149 (37%), 91 (21%), 89 (56%), 57 (21%), 53 (38%)

[EXAMPLE 16]

Synthesis of N,N-dimethyl[o-(N-allyl-2,6-dichloroanilino)phenyl]acetamide

Following the same procedure as in Example 6 except that dimethylamine was used in place of ammonia, N,N-dimethyl[o-(N-allyl-2,6-dichloroanilino)phenyl]acetamide was obtained.

The compound was identified by melting point, IR and NMR.

M.P.: 110°–114° C. (recrystallized from n-hexane)

IR(KBr) cm$^{-1}$: 3055, 2918, 2843, 1652, 1489, 1447, 1229, 784, 773

NMR(CDCl$_3$)δ ppm: 2.70 (3H, s), 2.80 (3H, s), 3.08 (2H, s), 4.26 (2H, dt, J=6 and 2 Hz), 5.11 (1H, dq, J=10 and 2Hz), 5.19 (1H, dq, J=17 and 2Hz), 5.93 (1H, ddt., J=17, 10 and 6 Hz), 6.90–7.25 (7H, m)

We claim:

1. An o-(N-allyl-2,6-dichloroanilino)phenylacetic acid derivative represented by the formula:

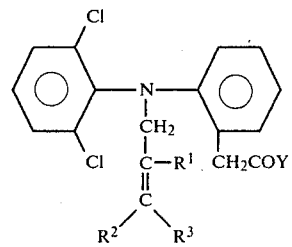

wherein R$^1$, R$^2$ and R$^3$, which may be the same or different, individually represent a hydrogen atom, a halogen atom or an alkyl group; Y represents a hydroxyl group, an alkoxyl group, a —OM$^1$ group in which M$^1$ is an alkali metal atom, a —OM$_{\frac{1}{2}}^2$ group in which M$^2$ is an alkaline earth metal atom, an amino group having the formula —NR$^5$R$^6$ in which R$^5$ and R$^6$, which may be the same or different, individually represent a hydrogen atom or an alkyl group, or a hydroxylamino group.

2. An o-(N-allyl-2,6-dichloroanilino)phenylacetic acid derivative according to claim 1 in which R$^1$, R$^2$ and R$^3$ individually represent a hydrogen atom, a chlorine atom or an alkyl group having 1 to 4 carbon atoms and R$^5$ and R$^6$ individually represent a hydrogen atom or an alkyl group having 1 to 4 carbon atoms.

3. An o-(N-allyl-2,6-dichloroanilino)phenylacetic acid derivative according to claim 2 in which R$^1$ represents a hydrogen atom or a methyl group, and R$^2$ and R$^3$ individually represent a hydrogen atom, a methyl group or a chlorine atom.

4. o-(N-Allyl-2,6-dichloroanilino)phenylacetic acid as claimed in claim 3.

5. o-(N-Crotyl-2,6-dichloroanilino)phenylacetic acid as claimed in claim 3.

6. Sodium o-(N-allyl-2,6-dichloroanilino)phenylacetate as claimed in claim 3.

7. Methyl o-(N-allyl-2,6-dichloroanilino)phenylacetate as claimed in claim 3.

8. Ethyl o-(N-allyl-2,6-dichloroanilino)phenylacetate as claimed in claim 3.

9. Methyl o-(N-methallyl-2,6-dichloroanilino)phenylacetate as claimed in claim 3.

10. Methyl o-(N-crotyl-2,6-dichloroanilino)phenylacetate as claimed in claim 3.

11. Methyl o-[N-(3-chloro-2-buten-1-yl)-2,6-dichloroanilino]phenylacetate as claimed in claim 3.

12. o-(N-Allyl-2,6-dichloroanilino)phenylacetamide as claimed in claim 3.

13. N,N-Dimethyl-o-(N-allyl-2,6-dichloroanilino)phenylacetamide as claimed in claim 3.

14. o-(N-Allyl-2,6-dichloroanilino)phenylacetohydroxamic acid as claimed in claim 3.

* * * * *